United States Patent
West (10) Patent No.: US 10,842,929 B2
(45) Date of Patent: Nov. 24, 2020

(54) CASSETTE PLATE OF CASSETTE HOLDER OF MEDICAL DEVICE AND TOOL-FREE METHODS OF INSTALLING AND REMOVING THE SAME

(71) Applicant: Fenwal, Inc., Lake Zurich, IL (US)

(72) Inventor: Richard L. West, Lake Villa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 16/710,024

(22) Filed: Dec. 11, 2019

(65) Prior Publication Data

US 2020/0188574 A1 Jun. 18, 2020

Related U.S. Application Data

(60) Provisional application No. 62/778,971, filed on Dec. 13, 2018.

(51) Int. Cl.
*A61M 1/36* (2006.01)

(52) U.S. Cl.
CPC ........ *A61M 1/3693* (2013.01); *A61M 1/3639* (2013.01); *A61M 2205/121* (2013.01); *A61M 2205/128* (2013.01); *A61M 2209/084* (2013.01)

(58) Field of Classification Search
CPC .............. A61M 1/3693; A61M 1/3639; A61M 2205/121
See application file for complete search history.

(56) References Cited

U.S. PATENT DOCUMENTS

| | | |
|---|---|---|
| 4,798,090 A | 1/1989 | Heath et al. |
| 5,868,696 A | 2/1999 | Floden |
| 7,935,074 B2 | 5/2011 | Plahey et al. |
| 8,758,288 B2 | 6/2014 | Manzella, Jr. et al. |
| 10,413,653 B2 | 9/2019 | Case et al. |
| 2003/0222029 A1* | 12/2003 | Muller ................ B04B 5/0442 210/739 |
| 2012/0061310 A1 | 3/2012 | Beden et al. |
| 2014/0178215 A1* | 6/2014 | Baxter ............... A61F 9/00745 417/360 |
| 2015/0083647 A1 | 3/2015 | Meyer et al. |

FOREIGN PATENT DOCUMENTS

| | | |
|---|---|---|
| WO | WO 1990/011305 A1 | 3/1999 |
| WO | WO 2014/099779 A1 | 6/2014 |

OTHER PUBLICATIONS

Extended European Search Report for Application No. 19215094.4 dated Apr. 17, 2020.

* cited by examiner

*Primary Examiner* — Krishnan S Menon
(74) *Attorney, Agent, or Firm* — Cook Alex Ltd.

(57) ABSTRACT

A cassette holder includes an actuator assembly and a cassette plate. The actuator assembly includes an actuator (e.g., a valve actuator or a sensing actuator) and a shaft, with the shaft including a head, a base, and a perimeter groove defined between the head and the base. The cassette plate includes an opening aligned with the actuator and a keyhole at least partially aligned with the shaft. The keyhole is associated with a channel of the cassette plate, which is configured to receive at least a portion of a lever. The lever is movable between a locked position (in which the lever is primarily positioned within the channel) preventing removal of the shaft from the keyhole and an unlocked position (in which the lever is primarily positioned outside of the channel) allowing for removal of the shaft from the keyhole.

23 Claims, 10 Drawing Sheets

CASSETTE PLATE OF CASSETTE HOLDER OF MEDICAL DEVICE AND TOOL-FREE METHODS OF INSTALLING AND REMOVING THE SAME

CROSS-REFERENCE TO RELATED APPLICATIONS

This application claims the benefit of and priority of U.S. Provisional Patent Application Ser. No. 62/778,971, filed Dec. 13, 2018, the contents of which are incorporated by reference herein.

BACKGROUND

Field of the Disclosure

The present disclosure relates to cassette holders of medical devices. More specifically, the present disclosure relates to cassette plates or carriers of cassette holders configured to be installed and removed without the use of tools.

Description of Related Art

Whole blood may routinely be separated into its various components, such as red blood cells, platelets, and plasma. Conventional blood processing methods may use durable separator equipment (including a centrifuge, for example) in association with single use, sterile processing sets, which are typically made of plastic. The configuration of the single use processing sets used in combination with different separator equipment may vary widely, but some sets may include a molded plastic piece commonly referred to as a cassette. As used herein, the term "cassette" refers to a component of a fluid processing system which includes a number of defined fluid pathways and valve stations. The cassette is commonly secured to a cassette holder of the durable equipment via motor-powered grippers or mechanical latches. The cassette holder may include actuators for opening and closing the valve stations, which determine which of the fluid pathways are connected to each other, thereby directing fluid between a number of sources and destinations. Exemplary fluid processing systems as well as their cassettes and cassette holders are described in greater detail in U.S. Pat. No. 5,868,696 and U.S. Patent Application Publication No. 2017/0290972, both of which are hereby incorporated herein by reference.

One of the components of a conventional cassette holder is the cassette plate or carrier, which positions, secures, and transports the cassette. From time to time, it may be necessary to remove the cassette plate, such as for cleaning, repair, or replacement. Installation and removal of conventional cassette plates requires the use of tools. The particular tools that are required to install and remove a cassette plate may vary according to the particular configuration of the cassette holder, but according to one known configuration, the cassette plate is secured to the cassette holder using screws or comparable mechanical fasteners, which requires the use of a screwdriver or the like for installation and removal of the cassette plate. As requiring the use of a tool to install and remove the cassette plate increases the time necessary to do so, it would be advantageous to provide a cassette holder and cassette plate allowing for the cassette plate to be installed and removed without the use of tools.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a cassette holder of a fluid processing system includes an actuator assembly and a cassette plate. The actuator assembly includes an actuator and a shaft, with the shaft having a head, a base, and a perimeter groove defined between the head and the base. The cassette plate includes a lever and defines a channel configured to receive at least a portion of the lever. The cassette plate also defines an opening aligned with the actuator and a keyhole associated with the channel, with the keyhole being at least partially aligned with the shaft and including a necked down portion at least partially positioned outside of the channel and an open portion. The open portion of the keyhole is configured to allow passage of the head of the shaft therethrough, while the necked down portion of the keyhole is configured to receive the perimeter groove of the shaft while preventing passage of the head of the shaft therethrough. The lever is movable between a locked position in which the lever is primarily positioned within the channel to prevent movement of the shaft from the necked down portion of the keyhole to the open portion of the keyhole and an unlocked position in which the lever is primarily positioned outside of the channel to allow movement of the shaft between the open portion of the keyhole and the necked down portion of the keyhole.

In another aspect, a method of associating a cassette plate to a cassette holder of a fluid processing system includes aligning a shaft of the cassette holder with an open portion of a keyhole of the cassette plate associated with a channel of the cassette plate. The cassette plate is moved toward the shaft so as to cause a head of the shaft to move through the open portion of the keyhole and position a perimeter groove of the shaft within the open portion of the keyhole. The cassette plate is moved with respect to the shaft so as to move the perimeter groove of the shaft from the open portion of the keyhole to a necked down portion of the keyhole configured to prevent passage of the head of the shaft therethrough. A lever associated with the channel of the cassette plate is moved from an unlocked position in which the lever is primarily positioned outside of the channel to a locked position in which the lever is primarily positioned within the channel to prevent movement of the shaft from the necked down portion of the keyhole to the open portion of the keyhole.

In yet another aspect, a method of removing a cassette plate from a cassette holder of a fluid processing system includes moving a lever of the cassette plate from a locked position in which the lever is primarily positioned within a channel of the cassette plate to an unlocked position in which the lever is primarily positioned outside of the channel. The cassette plate is moved with respect to a shaft of the cassette holder so as to move a perimeter groove of the shaft from a necked down portion of the keyhole to an open portion of the keyhole. The cassette plate is moved away from the shaft so as to cause a head of the shaft to move through the open portion of the keyhole.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
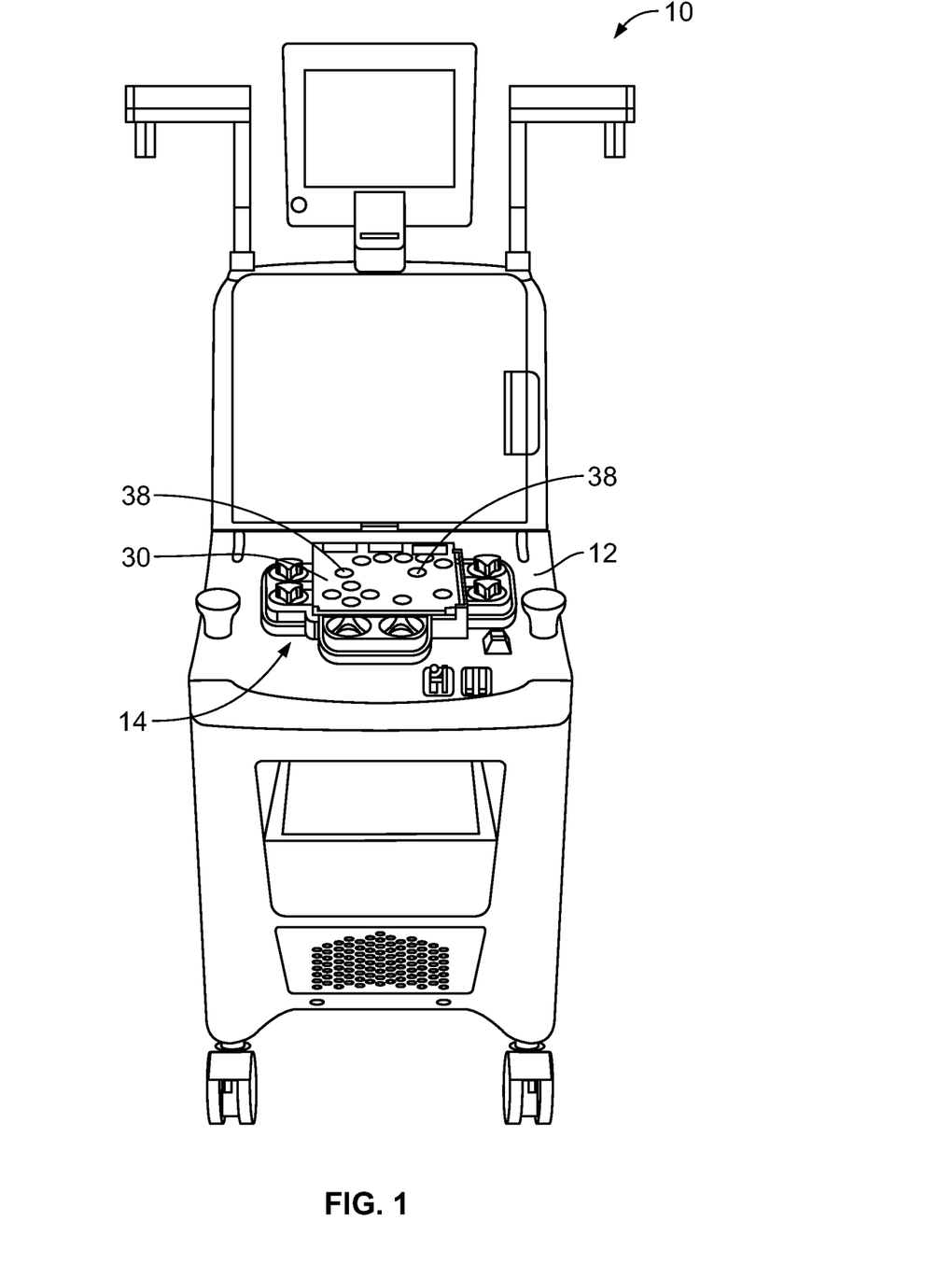
FIG. 1 is a front elevational view of an exemplary fluid processing system according to an aspect of the present disclosure.

FIG. 1 shows a fluid processing system 10 that can be used for processing various fluids, but may be particularly well suited for processing whole blood and other suspensions of biological cellular materials. The system 10 may include a device (such as a centrifuge or a spinning membrane) that is suitable for separating a fluid into two or more components based on the density and/or size of such components. The system 10 further includes a sloped front panel 12 having at least one loading area or cassette holder 14 (FIG. 2), which is configured to receive and grip a cassette 16 (FIGS. 3-6) of a disposable, single-use processing set. It should be understood that the illustrated fluid processing system 10 and cassette 16 are merely exemplary and that the configurations of the system 10 and cassette 16 may vary without departing from the scope of the present disclosure.

Figure 3:
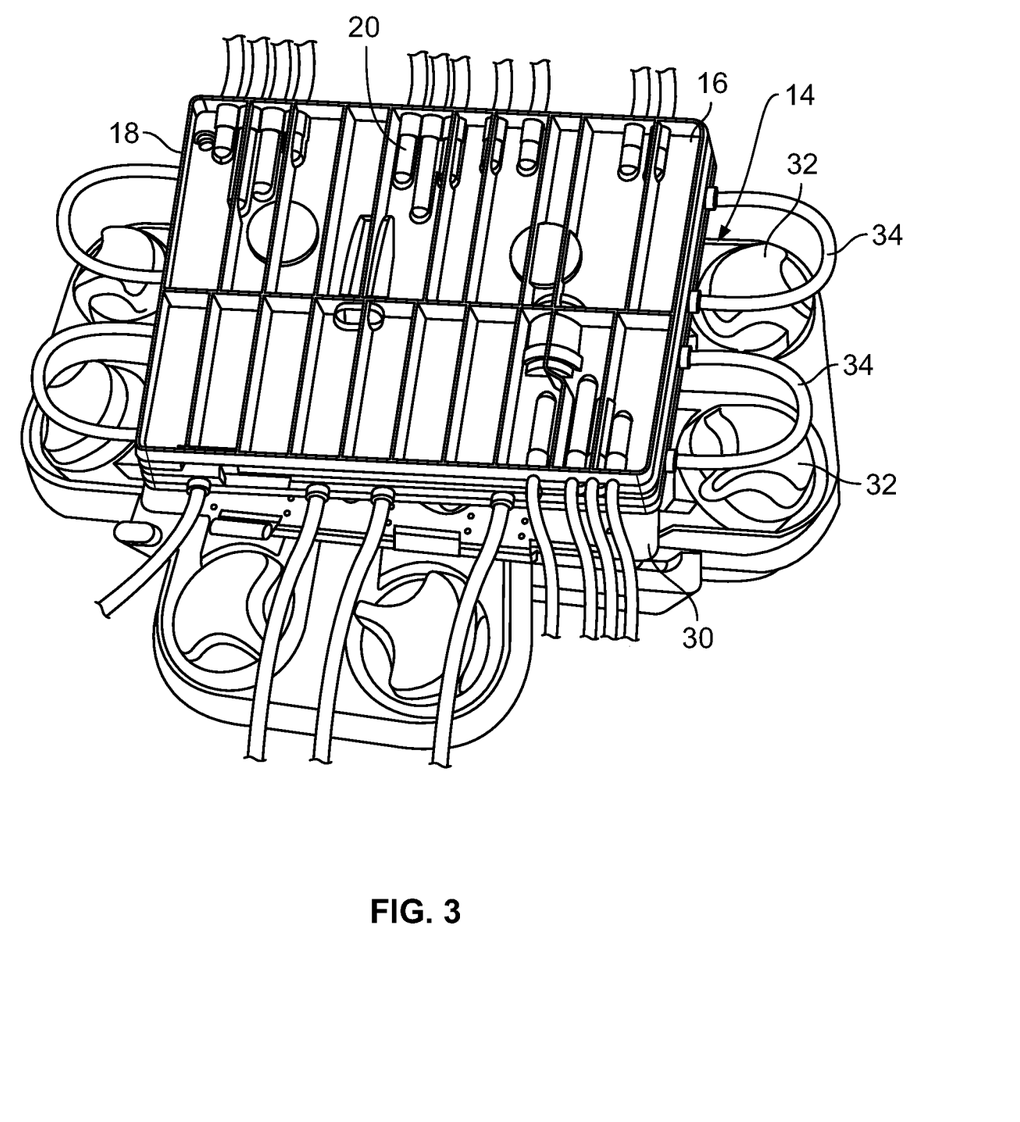
FIG. 3 is a top perspective view of a cassette prior to being mounted to the cassette holder of FIG. 2.
Figure 4:
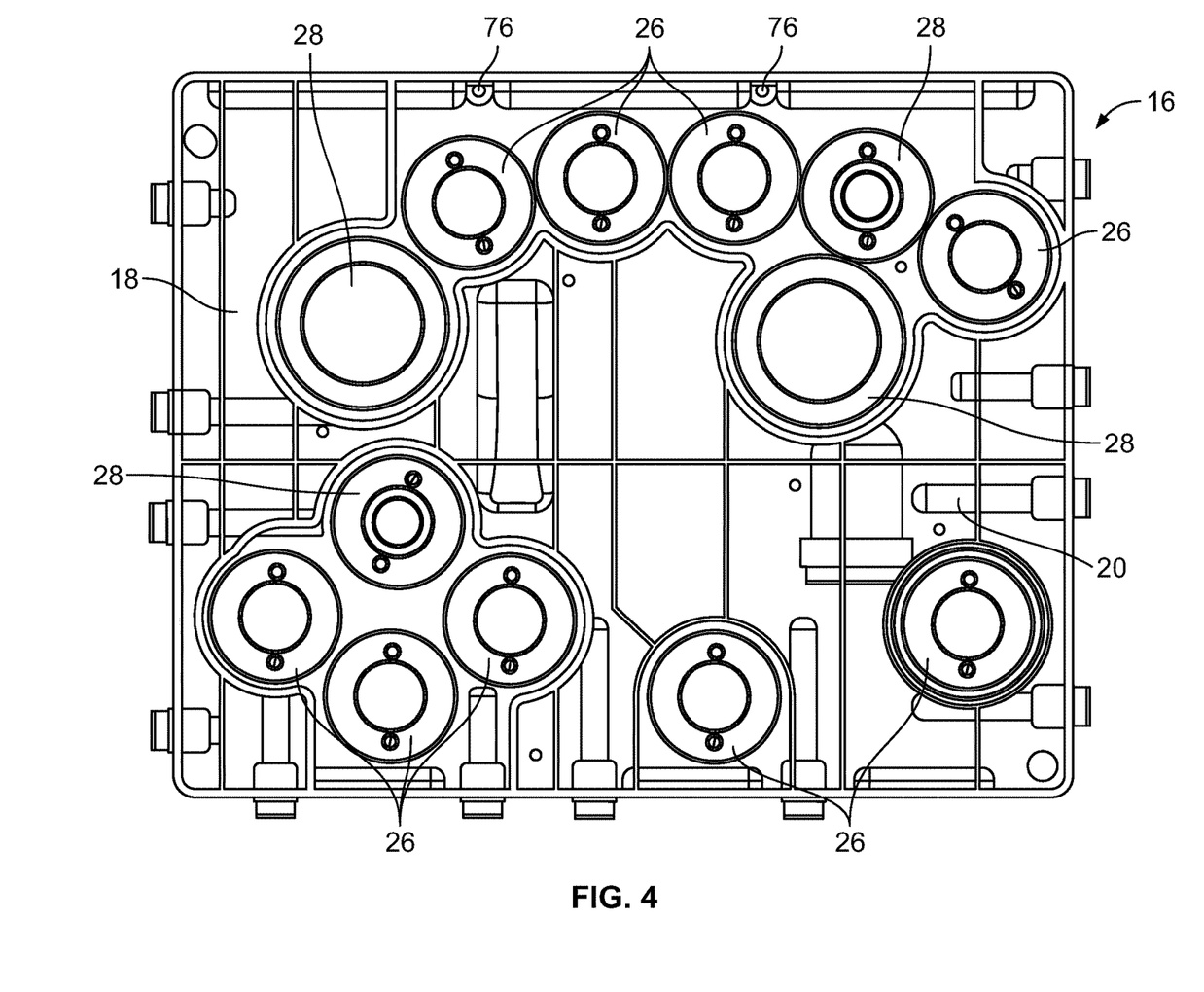
FIG. 4 is a top plan view of the defined pathways of the cassette of FIG. 3.

The cassette 16, as shown in FIGS. 3-6, may include an injection molded body 18 that may be compartmentalized to form a plurality of defined pathways 20 (FIG. 4). The body 18 may be covered by a top cover 22 and a bottom cover 24 (FIG. 6, enabling the cassette 16 and its fluid contents to be closed from the surrounding environment. For the purposes of description, the side of the cassette 16 facing away from the system 10 in use is considered to be the top of the cassette 16, while the opposing, bottom surface of the cassette 16 faces towards the system 10. In one embodiment, the cassette body 18 and the top cover 22 are formed of a rigid, medical grade material (e.g., a rigid plastic material), while the bottom cover 24 is configured as a diaphragm or membrane formed of a flexible sheet of medical grade material (e.g., a flexible plastic material).

Figure 5:
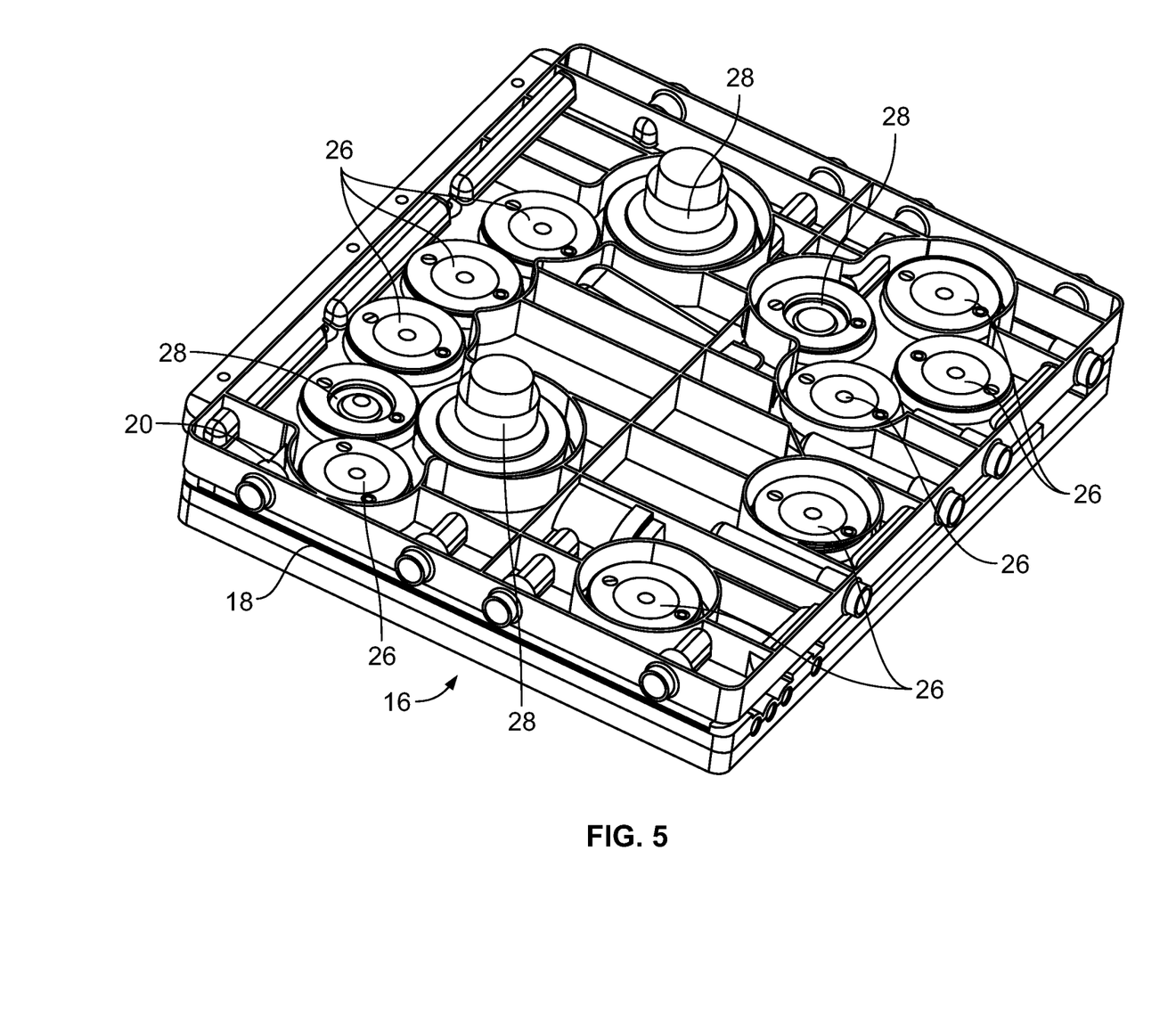
FIG. 5 is a bottom perspective view of the cassette of FIG. 3.

As shown in FIGS. 4 and 5, the bottom of the cassette body 18 may include an array of valve stations 26 disposed under and/or adjacent to certain locations of the various defined pathways 20 of the body 18. The bottom of the cassette body 18 may also define a plurality of pressure-sensing stations 28. The valve stations 26 and the pressure-sensing stations 28 may communicate with the various defined pathways 20 in a predetermined manner. The number, configuration, and/or arrangement of the valve stations 26 and the sensing stations 28 may vary without departing from the scope of the present disclosure.

Figure 2:
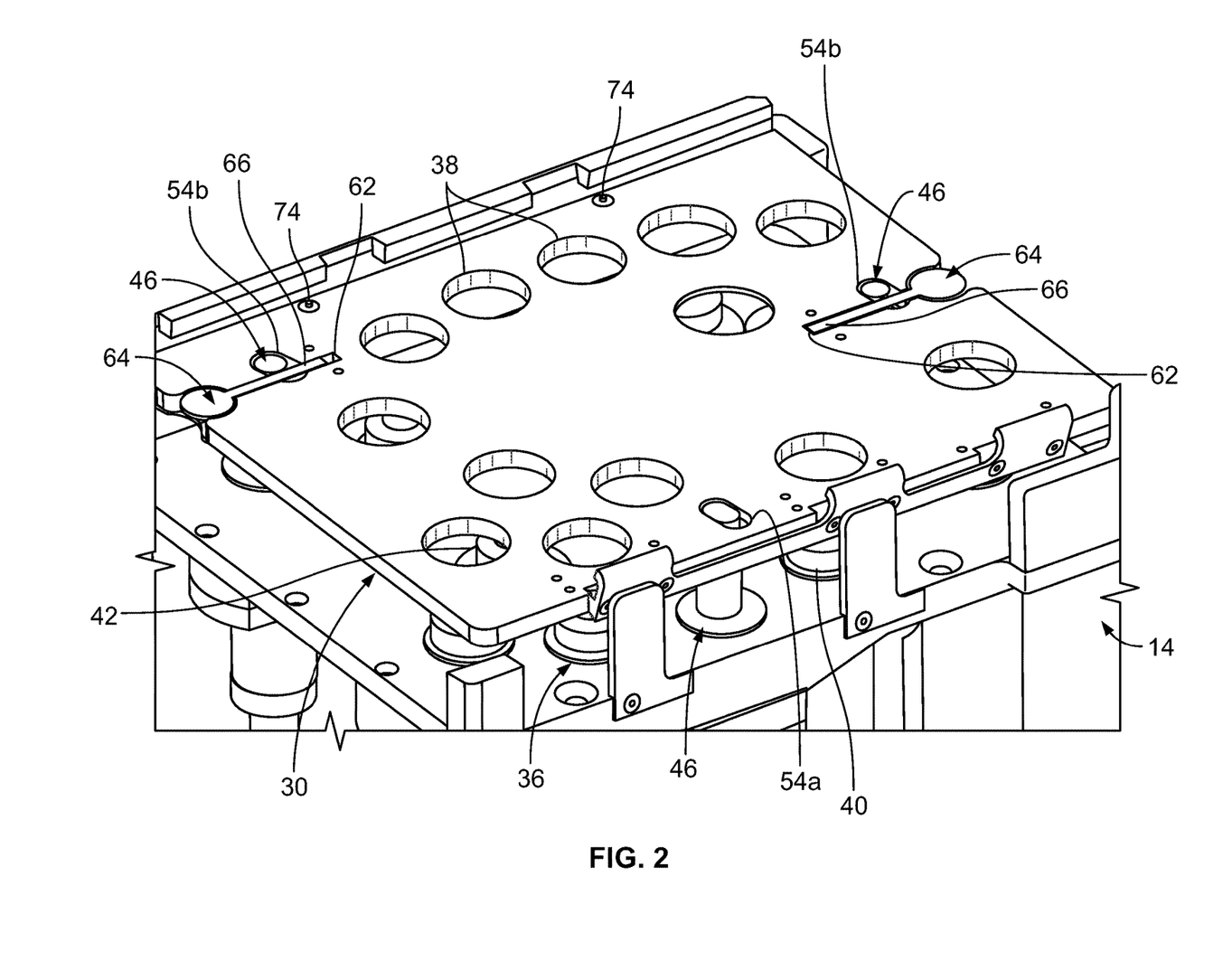
FIG. 2 is a top perspective view of a portion of a cassette holder of the fluid processing system of FIG. 1, with levers of a cassette plate of the cassette holder in a locked position.

The cassette holder 14 is configured to receive and grip the cassette 16 in a desired operating position, with the cassette 16 seated upon a cassette plate 30 of the cassette holder 14, as shown in FIGS. 2 and 3. The cassette holder 14 includes a pump mechanism configured to convey fluid through the pathways 20 of the cassette 16. In the embodiment of FIG. 3, the cassette holder 14 is shown as including a plurality of peristaltic pump stations 32. Each peristaltic pump station 32 is configured to receive a different tubing loop 34 extending from a sidewall of the cassette 16 for moving fluid through the tubing loops 34 and, hence, through the pathways 20 of the cassette 16 in fluid communication with the tubing loops 34. In other embodiments, other pump mechanisms may be employed without departing from the scope of the present disclosure. For example, the cassette body 18 may define one or more pump stations configured to be manipulated (e.g., by an actuator acting upon the flexible membrane overlaying the pump station) to convey fluid through the pathways 20 of the cassette 16.

The cassette holder 14 may be configured such that, when the cassette 16 has been loaded onto the cassette plate 30, the cassette holder 14 lowers the cassette 16 into contact with a valve and sensor assembly 36 of the cassette holder 14 (FIG. 2) located underneath the cassette plate 30. The cassette plate 30 may define a plurality of openings 38 to allow components of the valve and sensor assembly 36 to access the valve stations 26 and sensing stations 28 of the cassette 16 when the cassette 16 and cassette plate 30 have been lowered into association with the valve and sensor assembly 36. The illustrated valve and sensor assembly 36 includes valve actuators 40 and pressure-sensing actuators or transducers 42 configured to act in concert with the valve stations 26 and sensing stations 28 of the cassette 16 to direct and monitor fluid flow within the cassette 16. The valve actuators 40 and the pressure-sensing actuators or transducers 42 may be mutually arranged in the same layout as the valve stations 26 and sensing stations 28 on the bottom of the cassette 16.

Figure 6:
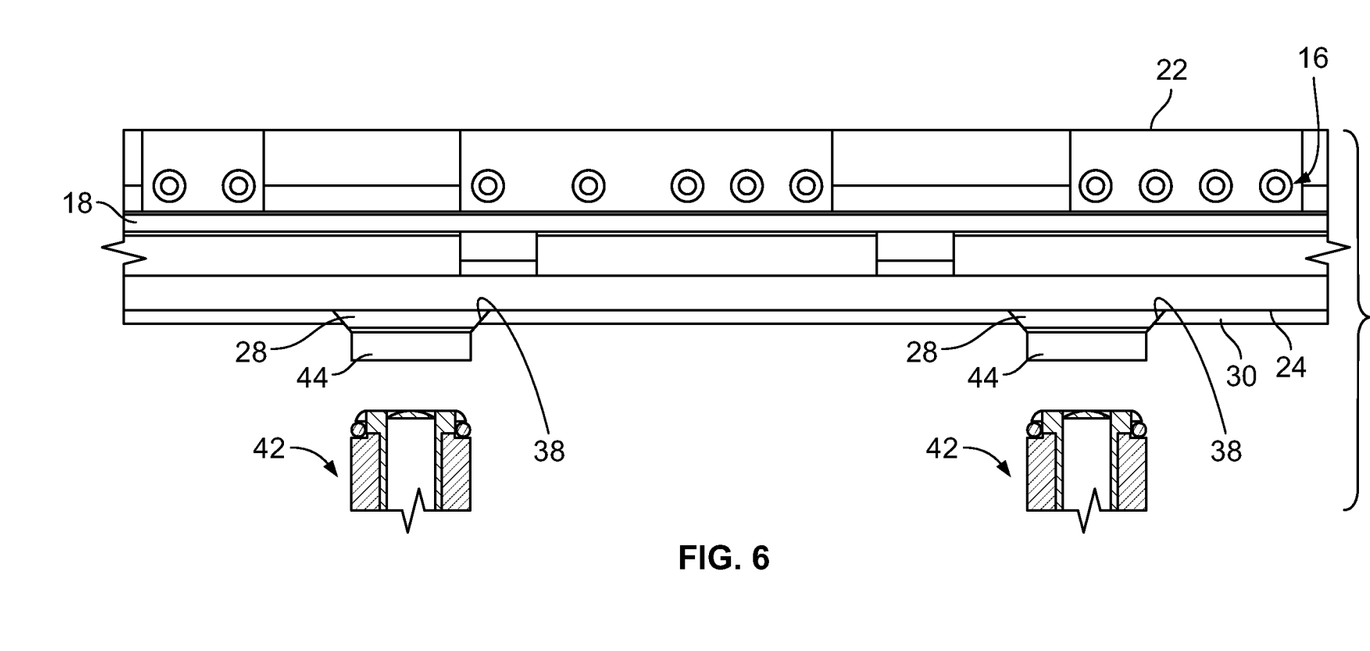
FIG. 6 is a cross-sectional view of the cassette of FIG. 3 prior to engagement with a valve and sensor assembly of the fluid processing system of FIG. 1.

FIG. 6 shows an elevational view of the cassette 16 seated on the cassette plate 30, prior to engagement with sensor actuators or transducers 42 that form a part of the valve and sensor assembly 36. The pressure sensing stations 28 of the cassette 16 are shown as including caps 44 extending from the bottom of the cassette 16. In such a configuration, when the cassette 16 is seated onto the cassette plate 30, the caps 44 extend beyond the plane of the cassette plate 30 via the openings 38 of the cassette plate 30. Each cap 44 may be configured to engage an associated sensor actuator or transducer 42, ensuring that an effective seal is created for proper pressure sensing at each pressure-sensing station 28.

Figure 8:
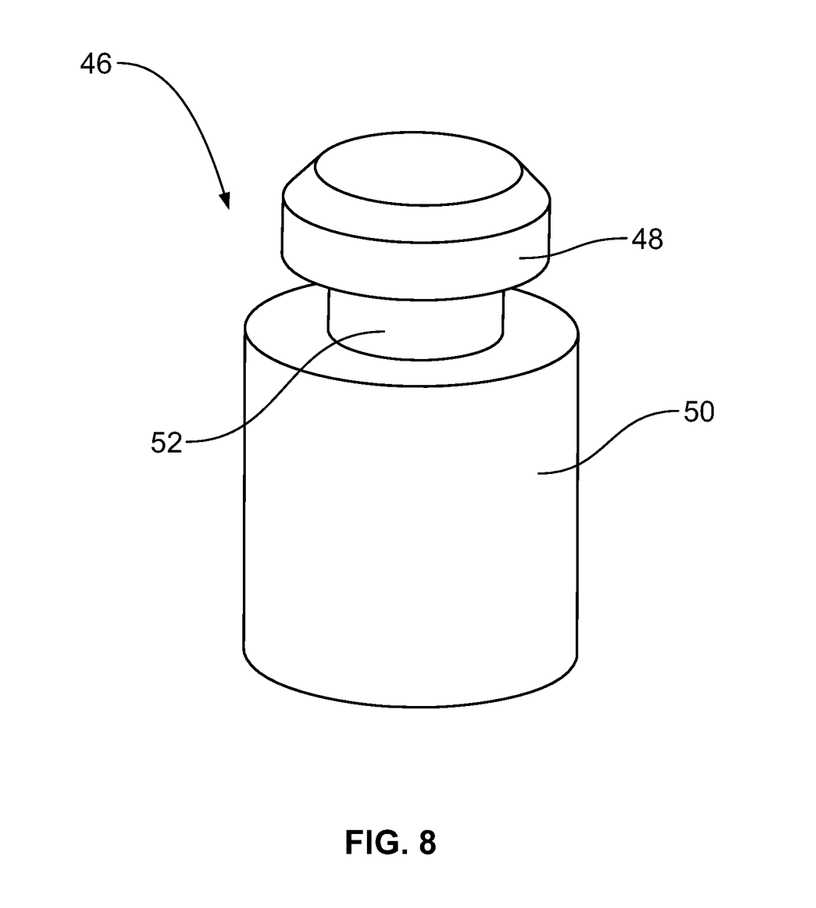
FIG. 8 is a perspective view of a shaft of the fluid processing system of FIG. 1.

In addition to the valve and sensor actuators 40 and 42, the valve and sensor assembly 36 further includes at least one shaft 46, with FIG. 2 illustrating three shafts 46. Each shaft 46 includes a head 48 and a base 50, with a perimeter groove or relief 52 separating the head 48 and the base 50, as shown in FIG. 8. In the illustrated embodiment, the shaft 46 is substantially cylindrical, but it is within the scope of the present disclosure for the shaft 46 to be differently configured (e.g., with a different cross-sectional shape). If the cassette plate 30 is configured to lower the cassette 16 into contact with the valve and sensor assembly 36, the shafts 46 may be configured for reciprocating motion to alternately draw the cassette 16 and cassette plate 30 downwardly toward the valve and sensor assembly 36 and lift the cassette 16 and cassette plate 30 upwardly away from the valve and sensor assembly 36.

The shaft 46 of FIG. 8 is shown as having a base 50 with a greater diameter and cross-sectional area than the head 48, but it is within the scope of the present disclosure for the head 48 to have a larger diameter or cross-sectional area than the base 50 or for the head 48 to have the same cross-sectional shape and size as the base 50. Regardless of the particular configurations of the associated head 48 and base 50, the perimeter groove 52 has a smaller dimension than both in a plane perpendicular to a central axis of the shaft 46, such as a smaller diameter or a smaller width. By such a configuration, the shaft 46 may be considered to have an enlarged head 48 and an enlarged base 50, which allows for a particular interaction between the shaft 46 and an associated keyhole 54a (FIGS. 9 and 10) of the cassette plate 30.

Figure 9:
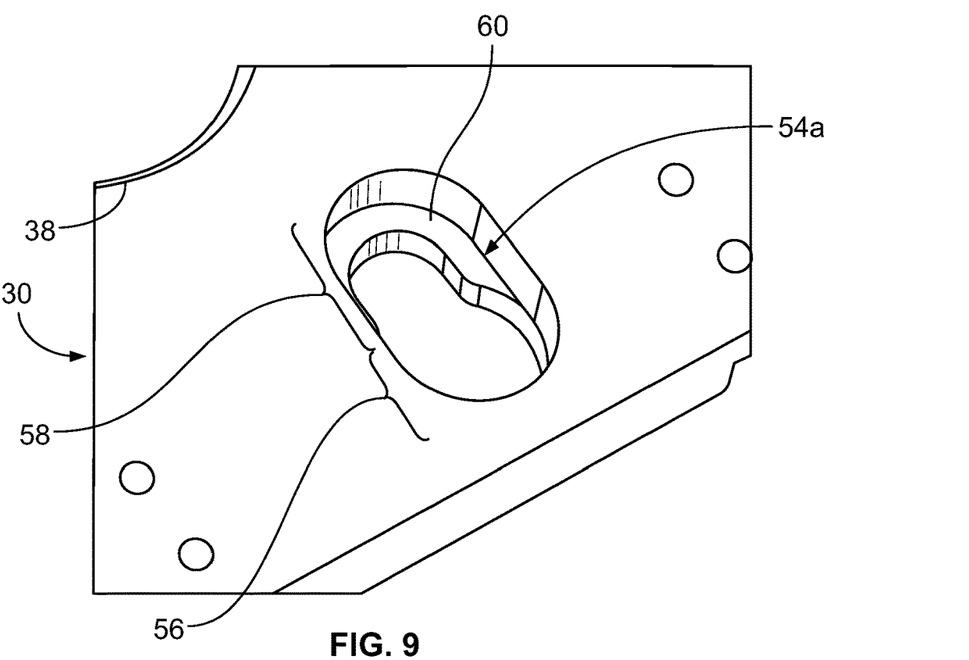
FIG. 9 is a detail view of a standalone keyhole of the cassette plate of FIG. 2.

The keyhole 54a of FIG. 9 includes an open portion 56 and a necked down portion 58. The open portion 56 is sized and configured to allow for the head 48 of an associated shaft 46 to pass therethrough. The perimeter groove 52 of the shaft 46 has a smaller dimension than the head 48, so it may also pass into or through the open portion 56 of the keyhole 54a. In the illustrated embodiment, the base 50 of the shaft 46 has a greater diameter or dimension or cross-sectional area than the head 48, such that the base 50 is incapable of moving into the open portion 56 of the keyhole 54a, thus limiting the movement of the cassette plate 30 along the shaft 46.

Figure 10:
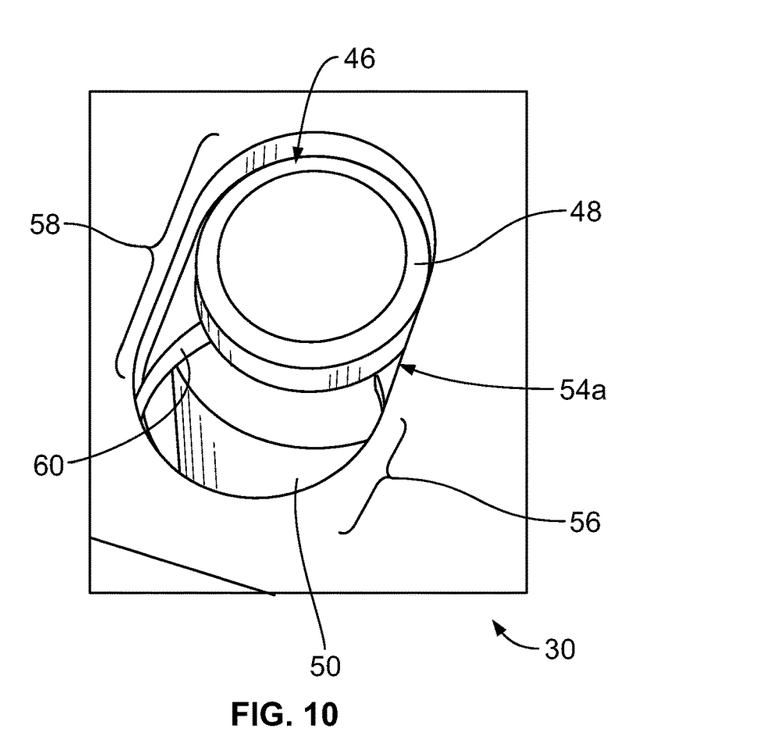
FIG. 10 is a detail view of the keyhole of FIG. 9, receiving a head of the shaft of FIG. 8.

The necked down portion 58 of the keyhole 54a includes a rim or lip 60 that provides the necked down portion 58 with a smaller dimension than the open portion 56 of the keyhole 54a. In the illustrated embodiment, the rim 60 reduces the width of the opening through the cassette plate 30, with the width of the opening defined by the rim 60 being less than the width of the head 48 of the shaft 46, but at least as great as the width of the perimeter groove 52 of the shaft 46. By such a configuration, the shaft 46 may be moved from the open portion 56 of the keyhole 54a to the necked down portion 58 (by moving the cassette plate 30 through a plane perpendicular to a central axis of the shaft 46), with at least a portion of the rim 60 being accommodated by the perimeter groove 52 of the shaft 46, the head 48 of the shaft 46 positioned above the rim 60, and the base 50 of the shaft 46 positioned below the rim 60 (FIG. 10). It may be advantageous for the distance between the top of the rim 60 and the upper surface of the cassette plate 30 to be no less than the height of the head 48 of the shaft 46 (as in FIG. 10), such that the head 48 remains below the upper surface of the cassette plate 30 to avoid interfering with mounting of a cassette 16 to the cassette plate 30. With the shaft 46 in the necked down portion 58 of the keyhole 54a, it becomes impossible to dissociate the cassette plate 30 from the rest of the cassette holder 14 without first moving the cassette plate 30 so as to place the shaft 46 into the open portion 56 of the keyhole 54a.

The keyhole 54a of FIGS. 9 and 10 is spaced away from channels 62 defined in the upper surface of the cassette plate 30, so it is referred to herein as a "standalone" keyhole. In the illustrated embodiment, there are keyholes 54b (which may be similarly configured to the standalone keyhole 54a) associated with each of two such channels 62, as can be seen in FIG. 2. If multiple keyholes 54 are provided, the valve and sensor assembly 36 includes the same number of shafts 46, with each shaft 46 being positioned to mate with a different one of the keyholes 54. Preferably, the keyholes 54 are similarly configured and oriented (i.e., with the open portion 56 of each keyhole 54 facing the same direction and the necked down portion 58 of each keyhole 54 facing the same direction), such that all of the shafts 46 simultaneously enter the open portion 56 of the associated keyhole 54, with the same movement of the cassette plate 30 thereafter moving each shaft 46 into the necked down portion 58 of the associated keyhole 54.

While the shaft 46 associated with the standalone keyhole 54a is free to move between the open and necked down portions 56 and 58 of the keyhole 54a, each channel 62 includes an associated lever 64 restricting the movement of the shaft 46 within the keyhole 54b. In particular, the levers 64 are separately movable between a locked position (FIGS. 2, 11, and 12) and an unlocked position (FIG. 7), with each lever 64 trapping the associated shaft 46 in the necked down portion 58 of the associated keyhole 54b or at least preventing the associated shaft 46 from moving to the open portion 56 of the associated keyhole 54b while the lever 64 is in the locked position (as will be described in greater detail herein).

The manner in which the levers 64 are movable between the locked and unlocked positions may vary without departing from the scope of the present disclosure, but in the illustrated embodiment, an end 66 of each lever 64 is pivotally connected to cassette plate 30 within the channel 62, such that the levers 64 pivot or rotate between the locked and unlocked positions. In such an embodiment, the channel 62 may extend to an edge 68 of the cassette plate 30 (with the two illustrated channels 62 extending to opposing edges 68), with the portion 70 of the edge 68 coinciding with the channel 64 being recessed (see FIGS. 11 and 12). A free end 72 of the lever 64 extends beyond the recessed portion 70 of the edge 68 to allow for an operator to reach through the recess and pull upon the free end 72 of the lever 64 from below to pivot the lever 64 from the locked position to the unlocked position. The free end 72 of the lever 64 may be enlarged compared to the rest of the lever 64 (as in the illustrated embodiment) or otherwise configured for improved handling by an operator. As in the illustrated embodiment, the free end 72 of the lever 64 may extend beyond the recessed portion 70 of the edge 68 without extending beyond portions of the edge 68 positioned adjacent to the recessed portion 70 to avoid increasing the size of the footprint of the cassette plate 30.

Figure 11:
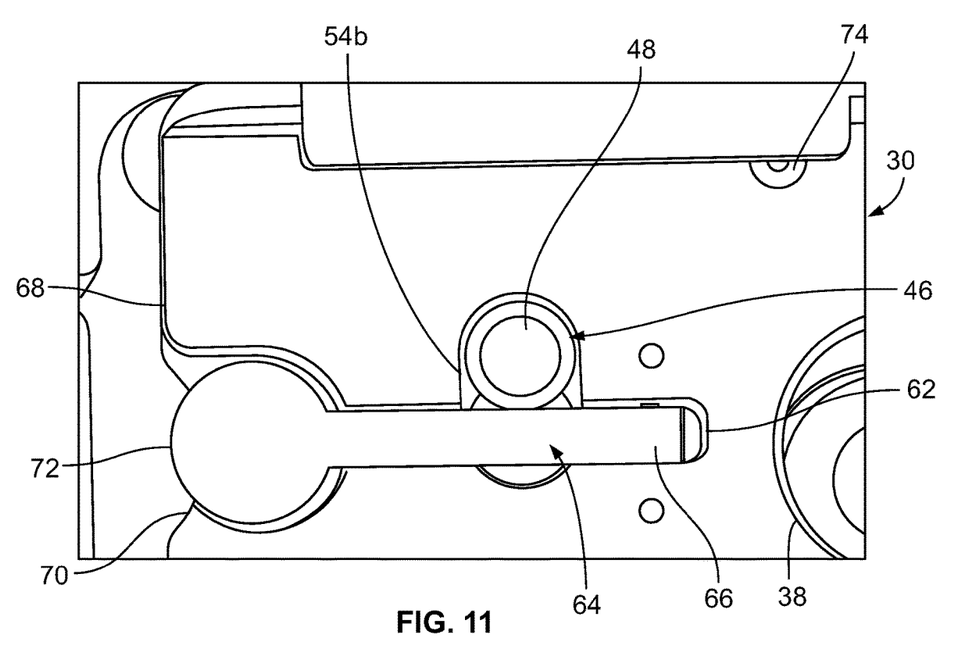
FIG. 11 is a detail view of one of the levers of the cassette plate of the cassette holder of FIG. 2.
Figure 12:
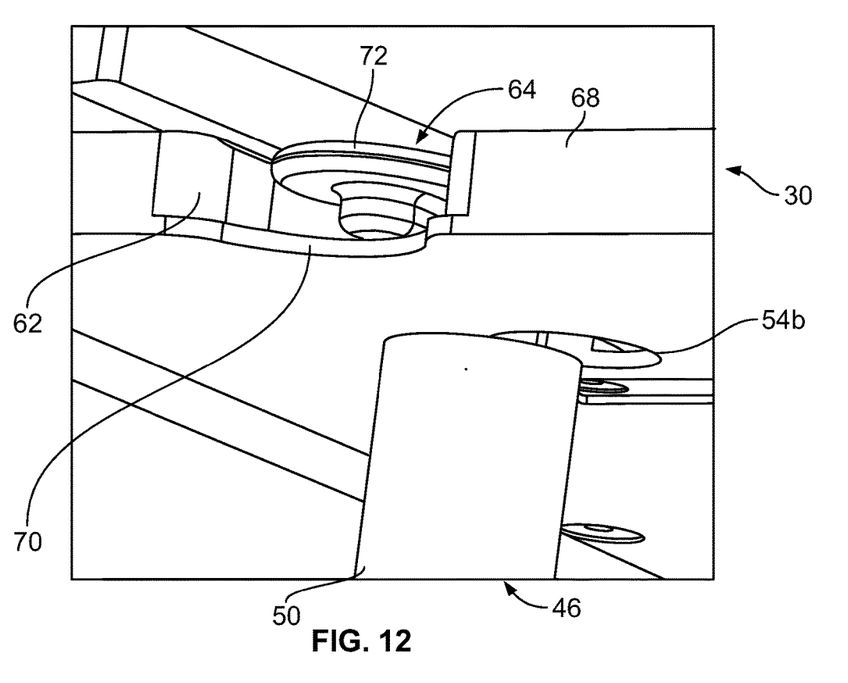
FIG. 12 is a bottom perspective view of the lever and an adjacent edge of the cassette plate of FIG. 11.

It should be understood that the particular configuration of the levers 64 and the manner in which they are moved between the locked and unlocked positions may vary without departing from the scope of the present disclosure, provided that the levers 64 are capable of selectively preventing and allowing an associated shaft 46 to move from the necked down portion 58 of an associated keyhole 54 to the open portion 56 of the keyhole 54. For example, rather than pivoting between the locked and unlocked positions, a lever could instead be moved within the plane defined by the cassette plate to move it between its locked and unlocked positions. This could include sliding the lever from its locked position (which may be the same as shown in FIGS. 2, 11, and 12) to an unlocked position in which a portion of the lever is received within a cavity associated with the channel and defined in the cassette plate, with the lever clear of the associated keyhole in the unlocked position. It is also within the scope of the present disclosure for a lever to be completely removed or separate from the cassette plate in its unlocked position, while being secured within the associated channel of the cassette plate (e.g., by a snap- or press-fit) in its locked position. Additionally, if a cassette plate includes a plurality of levers, it is within the scope of the present disclosure for the levers to be differently configured and/or to be moved between their locked and unlocked positions in different manners.

In the locked position, the lever 64 is primarily (if not completely) positioned within the associated channel 62 and extends at least partially (if not completely) across a portion of the associated keyhole 54b. In the illustrated embodiment the channel 62 extends through the center of the open portion 56 of the associated keyhole 54b, with the lever 64 covering the open portion 56 in the locked position (in the same plane as the head 48 of the shaft 46) and preventing the shaft 46 from being moved out of the necked down portion 58 of the keyhole 54b. In other embodiments, the open portion 56 of the keyhole 54b may be positioned on the opposite side of the channel 62 from the associated necked down portion 58, with the presence of the lever 64 in its locked position preventing the shaft 46 from being moved out of the necked down portion 58, across the channel 62, and into the open portion 56.

Figure 7:
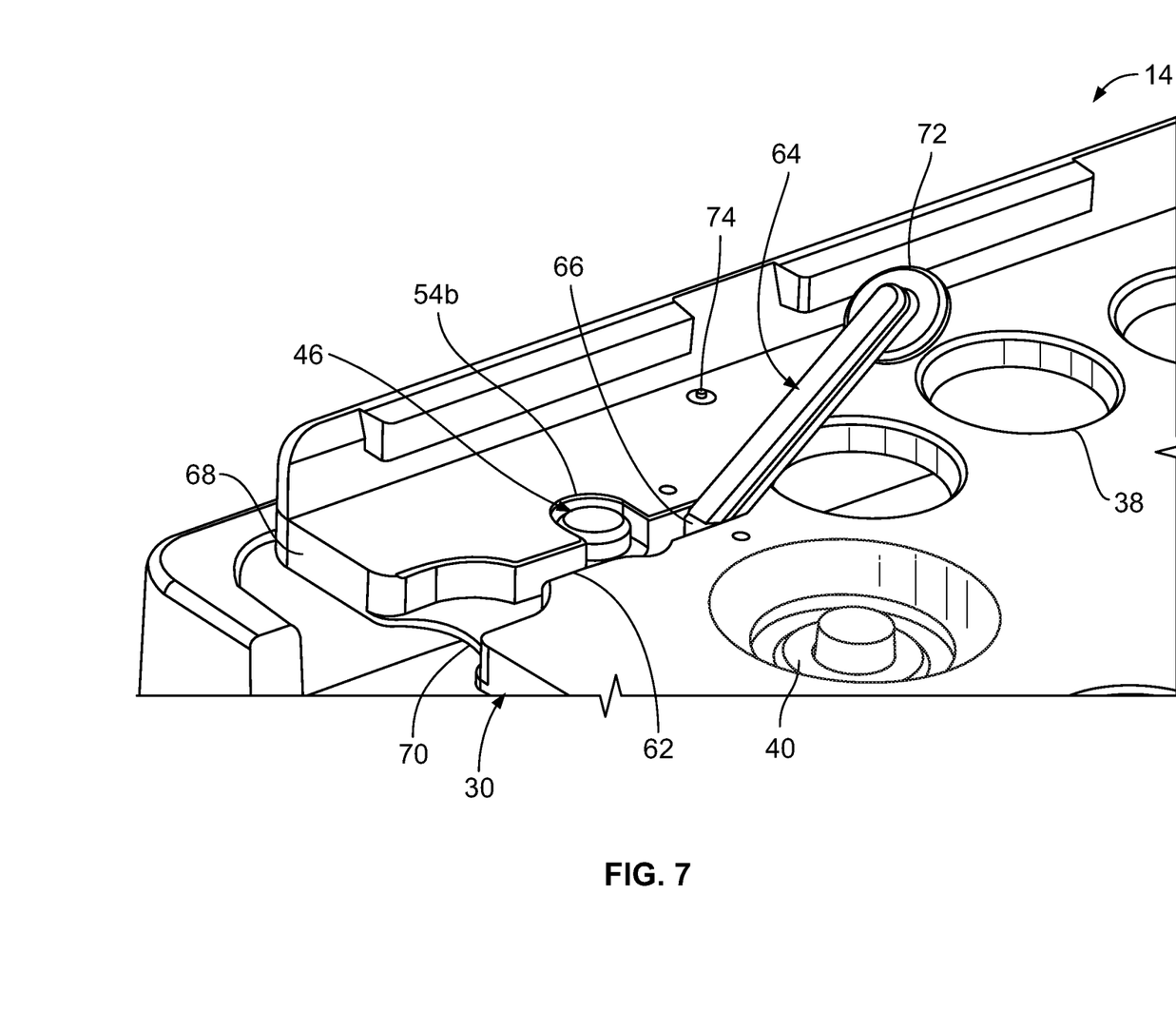
FIG. 7 is a top perspective view of a portion of the cassette holder of FIG. 2, with a lever of a cassette plate of the cassette holder in an unlocked position.

In the unlocked position, the lever 64 is spaced away from the associated keyhole 54b (preferably being primarily positioned outside of the channel 62, as in FIG. 7, in which the lever 64 is pivoted upwardly to extend above and outside of the channel 62). By separating the lever 64 from the associated keyhole 54b, the shaft 46 is free to move between the necked down and open portions 58 and 56 of the keyhole 54b, thus allowing for the cassette plate 30 to be dissociated from the shaft(s) 46 and from the other components of the cassette holder 14 for replacement, cleaning, maintenance, or the like.

It will be seen that, by such a configuration, the cassette plate 30 may be secured to and removed from the cassette holder 14 without the use of tools. For example, to install the cassette plate 30, the levers 64 are oriented to their unlocked positions (FIG. 7) and the open portions 56 of the keyholes 54 are aligned with and above the associated shafts 46 of the valve and sensor assembly 36. The cassette plate 30 is then moved toward the shafts 46, with the heads 48 of the shafts 46 extending into the open portions 56 of the keyholes 54. If the base 50 of a shaft 46 is larger than the open portion 56 of the associated keyhole 54, the base 50 will come into contact with the underside of the cassette plate 30, thus preventing over-insertion of the shaft 46 through the keyhole 54. The cassette plate 30 is then moved with respect to the shafts 46 to move each shaft 46 from the open portion 56 of the associate keyhole 54 to the necked down portion 58 (with a rim 60 of each necked down portion 58 being received by the perimeter groove 52 of the associated shaft 46). The levers 64 are then moved from their unlocked positions to their locked positions (FIGS. 2, 11, and 12) to prevent the shafts 46 from being moved out of the necked down portions 58 (and, thus, out of the keyholes 54), which secures the cassette plate 30 in place without the use of tools.

In one embodiment, the cassette holder 14 may be configured such that the levers 64 may not be moved from their unlocked position to their locked position without the cassette plate 30 being properly installed onto the valve and sensor assembly 36. This may be achieved by any suitable approach without departing from the scope of the present disclosure. In one embodiment, the necked down portion 58 of one or more of the keyholes 54 may include a button or latch. The button or latch is associated with the lever 64 paired to the keyhole 54 by an interconnect or linkage and may be associated with one or more of the other levers 64 of the cassette plate 30. Before the perimeter groove 52 of the corresponding shaft 46 is moved into the necked down portion 58 of the keyhole 54, the interconnect or linkage between the button or latch and the lever(s) 64 associated with the button or latch prevents movement of the lever(s) 64 from the unlocked position to the locked position (e.g., by engaging a portion of the lever(s) 64 or according to any suitable approach). Upon movement of the perimeter groove 52 of the shaft 46 into the necked down portion 58 of the keyhole 54, some portion of the shaft 46 (e.g., the head 48) will engage the button or latch. So engaging the button or latch will effect a change in the relationship between the interconnect or linkage and the lever(s) 64 (e.g., disengaging the interconnect or linkage from the lever(s) 64), thereby allowing the lever(s) to be moved from the unlocked position to the locked position. Such a configuration may be advantageous to ensure that a lever 64 is not in the locked position when attempting to secure the cassette plate 30 to the valve and sensor assembly 36, which would prevent the head 48 of the corresponding shaft 46 from being moved into the keyhole 54.

As shown in FIG. 7, the levers 64 may be configured to extend above the upper surface of the cassette plate 30 in their unlocked positions, thereby preventing association of a cassette 16 to the cassette plate 30 while in their unlocked positions. Accordingly, movement of the levers 64 from their unlocked positions to their locked positions not only serves to secure the cassette plate 30 to the valve and sensor assembly 36, but also allows for association of a cassette 16 to the cassette plate 30. Once a cassette 16 has been secured to the cassette plate 30, it will overlay the levers 64, thereby preventing the levers 64 from being moved from their locked positions to their unlocked positions.

To remove the cassette plate 30, the levers 64 are moved from their locked positions to their unlocked positions. The cassette plate 30 is moved with respect to the shafts 46 to move the shafts 46 from the necked down portions 58 of the associated keyholes 54 to the open portions 56. The cassette plate 30 is then pulled away from the shafts 46 to dissociate the shafts 46 from the cassette plate 30, thereby removing the cassette plate 30 from the other components of the cassette holder 14 without the use of tools.

The cassette plate 30 may include additional features without departing from the scope of the present disclosure. For example, in the illustrated embodiment, the upper surface of the cassette plate 30 includes a pair of ball detents 74 (FIG. 2). While two ball detents 74 are shown, it should be understood that a cassette plate 30 may have only one ball detent 74 or more than two ball detents 74 (if any). Additionally, while the ball detents 74 are shown as being arranged along a common edge of the upper surface of the cassette plate 30, it is also within the scope of the ball detents 74 to be positioned elsewhere. The ball detents 74 cooperate with formations 76 of the underside of the cassette 16 (FIG. 4) to offer feedback when the cassette 16 is being mounted to the cassette plate 30. In particular, the ball detents 74 are pressed downwardly into the cassette plate 30 when the underside or bottom cover 24 of the cassette 16 is pressed against the upper surface of the cassette plate 30 without aligning the ball detents 74 with the cassette formations 76. Once the cassette 16 has been moved to align the ball detents 74 and the cassette formations 76, the ball detents 74 will resiliently move upwardly to be partially received by the formations 76. Once the ball detents 74 have been received by the formations 76, they may help to keep the cassette 16 in place without sliding downwards.

Aspects

Aspect 1. A cassette holder of a fluid processing system, comprising: an actuator assembly comprising an actuator, and a shaft including a head, a base, and a perimeter groove defined between the head and the base; and a cassette plate including a lever and defining a channel configured to receive at least a portion of the lever, an opening aligned with the actuator, and a keyhole associated with the channel, at least partially aligned with the shaft, and including a necked down portion at least partially positioned outside of the channel and an open portion, wherein the open portion of the keyhole is configured to allow passage of the head of the shaft therethrough, the necked down portion of the keyhole is configured to receive the perimeter groove of the shaft while preventing passage of the head of the shaft therethrough, and the lever is movable between a locked position in which the lever is primarily positioned within the channel to prevent movement of the shaft from the necked down portion of the keyhole to the open portion of the keyhole and an unlocked position in which the lever is primarily positioned outside of the channel to allow movement of the shaft between the open portion of the keyhole and the necked down portion of the keyhole.

Aspect 2. The cassette holder of Aspect 1, wherein the open portion of the keyhole is at least partially positioned within the channel.

Aspect 3. The cassette holder of any one of the preceding Aspects, wherein the lever is configured to overlay the open portion of the keyhole in the locked position.

Aspect 4. The cassette holder of any one of the preceding Aspects, wherein the lever is spaced away from the open portion of the keyhole in the unlocked position.

Aspect 5. The cassette holder of any one of the preceding Aspects, wherein the lever is pivotal between the locked and unlocked positions.

Aspect 6. The cassette holder of any one of the preceding Aspects, wherein the channel extends to an edge of the cassette plate, the portion of the edge of the cassette plate associated with the channel is recessed, and in the locked position, an end of the lever extends beyond the recessed portion of the edge without extending beyond portions of the edge positioned adjacent to the recessed portion.

Aspect 7. The cassette holder of any one of the preceding Aspects, wherein the actuator assembly comprises a second shaft including a head, a base, and a perimeter groove defined between the head and the base of the second shaft, and the cassette plate includes a second lever and defines a second channel configured to receive at least a portion of the second lever, and a second keyhole associated with the second channel, at least partially aligned with the second shaft, and including a necked down portion at least partially positioned outside of the second channel and an open portion, the open portion of the second keyhole is configured to receive the perimeter groove of the second shaft while preventing passage of the head of the second shaft therethrough, the necked down portion of the second keyhole is configured to receive the perimeter groove of the second shaft while preventing passage of the head of the second shaft therethrough, and the second lever is movable between a locked position in which the second lever is primarily positioned within the second channel to prevent movement of the second shaft from the necked down portion of the second keyhole to the open portion of the second keyhole and an unlocked position in which the second lever is primarily positioned outside of the second channel to allow movement of the second shaft between the open portion of the second keyhole and the necked down portion of the second keyhole.

Aspect 8. The cassette holder of Aspect 7, wherein the channels extend to opposing edges of the cassette plate.

Aspect 9. The cassette holder of any one of the preceding Aspects, wherein the actuator assembly comprises a standalone shaft including a head, a base, and a perimeter groove defined between the head and the base of the standalone shaft, the cassette plate defines a standalone keyhole at least partially aligned with the standalone shaft and including a necked down portion and an open portion, the open portion of the standalone keyhole is configured to receive the perimeter groove of the standalone shaft while preventing passage of the head of the standalone shaft therethrough, the necked down portion of the standalone keyhole is configured to receive the perimeter groove of the standalone shaft while preventing passage of the head of the standalone shaft therethrough, and the standalone keyhole is not associated with any channel or lever of the cassette holder.

Aspect 10. The cassette holder of any one of the preceding Aspects, wherein the cassette plate further includes at least one ball detent configured to be contacted by a cassette mounted to the cassette holder.

Aspect 11. The cassette holder of any one of the preceding Aspects, wherein the cassette plate is configured to prevent movement of the lever from the unlocked position to the locked position when the perimeter groove of the shaft is not received by the necked down portion of the keyhole.

Aspect 12. A method of associating a cassette plate to a cassette holder of a fluid processing system, comprising: aligning a shaft of the cassette holder with an open portion of a keyhole of the cassette plate associated with a channel of the cassette plate; moving the cassette plate toward the shaft so as to cause a head of the shaft to move through the open portion of the keyhole and position a perimeter groove of the shaft within the open portion of the keyhole; moving the cassette plate with respect to the shaft so as to move the perimeter groove of the shaft from the open portion of the keyhole to a necked down portion of the keyhole configured to prevent passage of the head of the shaft therethrough; and moving a lever associated with the channel of the cassette plate from an unlocked position in which the lever is primarily positioned outside of the channel to a locked position in which the lever is primarily positioned within the channel to prevent movement of the shaft from the necked down portion of the keyhole to the open portion of the keyhole.

Aspect 13. The method of Aspect 12, wherein said moving the lever from the unlocked position to the locked position includes causing the lever to overlay the open portion of the keyhole.

Aspect 14. The method of any one of Aspects 12-13, wherein said moving the lever from the unlocked position to the locked position includes pivoting the lever from the unlocked position to the locked position.

Aspect 15. The method of any one of Aspects 12-14, wherein said moving the cassette plate with respect to the shaft includes moving the cassette plate through a plane perpendicular to a central axis of the shaft.

Aspect 16. The method of any one of Aspects 12-15, wherein the cassette holder includes a second shaft, the cassette plate defines a second keyhole associated with a second channel of the cassette plate, said aligning the shaft of the cassette holder with the open portion of the keyhole includes aligning the second shaft with an open portion of the second keyhole, said moving the cassette plate toward the shaft includes moving the cassette plate toward the second shaft so as to cause a head of the second shaft to move through the open portion of the second keyhole and position a perimeter groove of the second shaft within the open portion of the second keyhole, and said moving the cassette plate with respect to the shaft includes moving the cassette plate with respect to the second shaft so as to move the perimeter groove of the second shaft from the open portion of the second keyhole to a necked down portion of the second keyhole configured to prevent passage of the head of the second shaft therethrough, and further comprising moving a second lever associated with the second channel of the cassette plate from an unlocked position in which the second lever is primarily positioned outside of the second channel to a locked position in which the second lever is primarily positioned within the second channel to prevent movement of the second shaft from the necked down portion of the second keyhole to the open portion of the second keyhole.

Aspect 17. The method of any one of Aspects 12-16, wherein the cassette holder includes a standalone shaft, the cassette plate defines a standalone keyhole not associated with any channel or lever of the cassette holder, said aligning the shaft of the cassette holder with the open portion of the keyhole includes aligning the standalone shaft with an open portion of the standalone keyhole, said moving the cassette plate toward the shaft includes moving the cassette plate toward the standalone shaft so as to cause a head of the standalone shaft to move through the open portion of the standalone keyhole and position a perimeter groove of the standalone shaft within the open portion of the standalone keyhole, and said moving the cassette plate with respect to the shaft includes moving the cassette plate with respect to the standalone shaft so as to move the perimeter groove of the standalone shaft from the open portion of the standalone keyhole to a necked down portion of the standalone keyhole configured to prevent passage of the head of the standalone shaft therethrough.

Aspect 18. A method of removing a cassette plate from a cassette holder of a fluid processing system, comprising: moving a lever of the cassette plate from a locked position in which the lever is primarily positioned within a channel of the cassette plate to an unlocked position in which the lever is primarily positioned outside of the channel; moving the cassette plate with respect to a shaft of the cassette holder so as to move a perimeter groove of the shaft from a necked down portion of the keyhole to an open portion of the keyhole; and moving the cassette plate away from the shaft so as to cause a head of the shaft to move through the open portion of the keyhole.

Aspect 19. The method of Aspect 18, wherein said moving the lever from the locked position to the unlocked position includes moving the lever out of alignment with the open portion of the keyhole.

Aspect 20. The method of any one of Aspects 18-19, wherein said moving the lever from the locked position to the unlocked position includes pivoting the lever from the locked position to the unlocked position.

Aspect 21. The method of any one of Aspects 18-20, wherein said moving the cassette plate with respect to the shaft includes moving the cassette plate through a plane perpendicular to a central axis of the shaft.

Aspect 22. The method of any one of Aspects 18-21, wherein the cassette holder includes a second shaft, the cassette plate defines a second keyhole associated with a second channel of the cassette plate, said moving the lever of the cassette plate from the locked position to the unlocked position includes also moving a second lever associated with the second channel of the cassette plate from a locked position in which the second lever is primarily positioned within the second channel to an unlocked position in which the second lever is primarily positioned outside of the second channel, said moving the cassette plate with respect to the shaft includes moving the cassette plate with respect to the second shaft so as to move a perimeter groove of the second shaft from the necked down portion of the second keyhole to an open portion of the second keyhole, and said moving the cassette plate away from the shaft includes moving the cassette plate away from the second shaft so as to cause a head of the second shaft to move through the open portion of the second keyhole.

Aspect 23. The method of any one of Aspects 18-22, wherein the cassette holder includes a standalone shaft, the cassette plate defines a standalone keyhole not associated with any channel or lever of the cassette holder, said moving the cassette plate with respect to the shaft includes moving the cassette plate with respect to the standalone shaft so as to move a perimeter groove of the standalone shaft from the necked down portion of the standalone keyhole to an open portion of the standalone keyhole, and said moving the cassette plate away from the shaft includes moving the cassette plate away from the standalone shaft so as to cause a head of the standalone shaft to move through the open portion of the standalone keyhole.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A cassette holder of a fluid processing system, comprising:
an actuator assembly comprising
an actuator, and
a shaft including a head, a base, and a perimeter groove defined between the head and the base; and
a cassette plate including a lever and defining
a channel configured to receive at least a portion of the lever,
an opening aligned with the actuator, and
a keyhole associated with the channel, at least partially aligned with the shaft, and including a necked down portion at least partially positioned outside of the channel and an open portion, wherein
the open portion of the keyhole is configured to allow passage of the head of the shaft therethrough,
the necked down portion of the keyhole is configured to receive the perimeter groove of the shaft while preventing passage of the head of the shaft therethrough, and the lever is movable between a locked position in which the lever is primarily positioned within the channel to prevent movement of the shaft from the necked down portion of the keyhole to the open portion of the keyhole and an unlocked position in which the lever is primarily positioned outside of the channel to allow movement of the shaft between the open portion of the keyhole and the necked down portion of the keyhole.

2. The cassette holder of claim 1, wherein the open portion of the keyhole is at least partially positioned within the channel.

3. The cassette holder of claim 1, wherein the lever is configured to overlay the open portion of the keyhole in the locked position.

4. The cassette holder of claim 1, wherein the lever is spaced away from the open portion of the keyhole in the unlocked position.

5. The cassette holder of claim 1, wherein the lever is pivotal between the locked and unlocked positions.

6. The cassette holder of claim 1, wherein
the channel extends to an edge of the cassette plate,
the portion of the edge of the cassette plate associated with the channel is recessed, and
in the locked position, an end of the lever extends beyond the recessed portion of the edge without extending beyond portions of the edge positioned adjacent to the recessed portion.

7. The cassette holder of claim 1, wherein
the actuator assembly comprises a second shaft including a head, a base, and a perimeter groove defined between the head and the base of the second shaft, and
the cassette plate includes a second lever and defines
a second channel configured to receive at least a portion of the second lever, and
a second keyhole associated with the second channel, at least partially aligned with the second shaft, and including a necked down portion at least partially positioned outside of the second channel and an open portion,
the open portion of the second keyhole is configured to receive the perimeter groove of the second shaft while preventing passage of the head of the second shaft therethrough,
the necked down portion of the second keyhole is configured to receive the perimeter groove of the second shaft while preventing passage of the head of the second shaft therethrough, and
the second lever is movable between a locked position in which the second lever is primarily positioned within the second channel to prevent movement of the second shaft from the necked down portion of the second keyhole to the open portion of the second keyhole and an unlocked position in which the second lever is primarily positioned outside of the second channel to allow movement of the second shaft between the open portion of the second keyhole and the necked down portion of the second keyhole.

8. The cassette holder of claim 7, wherein the channels extend to opposing edges of the cassette plate.

9. The cassette holder of claim 1, wherein
the actuator assembly comprises a standalone shaft including a head, a base, and a perimeter groove defined between the head and the base of the standalone shaft,
the cassette plate defines a standalone keyhole at least partially aligned with the standalone shaft and including a necked down portion and an open portion,
the open portion of the standalone keyhole is configured to receive the perimeter groove of the standalone shaft while preventing passage of the head of the standalone shaft therethrough,
the necked down portion of the standalone keyhole is configured to receive the perimeter groove of the standalone shaft while preventing passage of the head of the standalone shaft therethrough, and
the standalone keyhole is not associated with any channel or lever of the cassette holder.

10. The cassette holder of claim 1, wherein the cassette plate further includes at least one ball detent configured to be contacted by a cassette mounted to the cassette holder.

11. The cassette holder of claim 1, wherein the cassette plate is configured to prevent movement of the lever from the unlocked position to the locked position when the perimeter groove of the shaft is not received by the necked down portion of the keyhole.

12. A method of associating a cassette plate to a cassette holder of a fluid processing system, comprising:
aligning a shaft of the cassette holder with an open portion of a keyhole of the cassette plate associated with a channel of the cassette plate;
moving the cassette plate toward the shaft so as to cause a head of the shaft to move through the open portion of the keyhole and position a perimeter groove of the shaft within the open portion of the keyhole;
moving the cassette plate with respect to the shaft so as to move the perimeter groove of the shaft from the open portion of the keyhole to a necked down portion of the keyhole configured to prevent passage of the head of the shaft therethrough; and
moving a lever associated with the channel of the cassette plate from an unlocked position in which the lever is primarily positioned outside of the channel to a locked position in which the lever is primarily positioned within the channel to prevent movement of the shaft from the necked down portion of the keyhole to the open portion of the keyhole.

13. The method of claim 12, wherein said moving the lever from the unlocked position to the locked position includes causing the lever to overlay the open portion of the keyhole.

14. The method of claim 12, wherein said moving the lever from the unlocked position to the locked position includes pivoting the lever from the unlocked position to the locked position.

15. The method of claim 12, wherein said moving the cassette plate with respect to the shaft includes moving the cassette plate through a plane perpendicular to a central axis of the shaft.

16. The method of claim 12, wherein
the cassette holder includes a second shaft,
the cassette plate defines a second keyhole associated with a second channel of the cassette plate,
said aligning the shaft of the cassette holder with the open portion of the keyhole includes aligning the second shaft with an open portion of the second keyhole,
said moving the cassette plate toward the shaft includes moving the cassette plate toward the second shaft so as to cause a head of the second shaft to move through the open portion of the second keyhole and position a perimeter groove of the second shaft within the open portion of the second keyhole, and said moving the cassette plate with respect to the shaft includes moving the cassette plate with respect to the second shaft so as to move the perimeter groove of the second shaft from the open portion of the second keyhole to a necked down portion of the second keyhole configured to prevent passage of the head of the second shaft therethrough, and further comprising moving a second lever associated with the second channel of the cassette plate from an unlocked position in which the second lever is primarily positioned outside of the second channel to a locked position in which the second lever is primarily positioned within the second channel to prevent movement of the second shaft from the necked down portion of the second keyhole to the open portion of the second keyhole.

17. The method of claim 12, wherein
the cassette holder includes a standalone shaft,
the cassette plate defines a standalone keyhole not associated with any channel or lever of the cassette holder,
said aligning the shaft of the cassette holder with the open portion of the keyhole includes aligning the standalone shaft with an open portion of the standalone keyhole,
said moving the cassette plate toward the shaft includes moving the cassette plate toward the standalone shaft so as to cause a head of the standalone shaft to move through the open portion of the standalone keyhole and position a perimeter groove of the standalone shaft within the open portion of the standalone keyhole, and
said moving the cassette plate with respect to the shaft includes moving the cassette plate with respect to the standalone shaft so as to move the perimeter groove of the standalone shaft from the open portion of the standalone keyhole to a necked down portion of the standalone keyhole configured to prevent passage of the head of the standalone shaft therethrough.

18. A method of removing a cassette plate from a cassette holder of a fluid processing system, comprising:
moving a lever of the cassette plate from a locked position in which the lever is primarily positioned within a channel of the cassette plate to an unlocked position in which the lever is primarily positioned outside of the channel;
moving the cassette plate with respect to a shaft of the cassette holder so as to move a perimeter groove of the shaft from a necked down portion of a keyhole to an open portion of the keyhole; and
moving the cassette plate away from the shaft so as to cause a head of the shaft to move through the open portion of the keyhole.

19. The method of claim 18, wherein said moving the lever from the locked position to the unlocked position includes moving the lever out of alignment with the open portion of the keyhole.

20. The method of claim 18, wherein said moving the lever from the locked position to the unlocked position includes pivoting the lever from the locked position to the unlocked position.

21. The method of claim 18, wherein said moving the cassette plate with respect to the shaft includes moving the cassette plate through a plane perpendicular to a central axis of the shaft.

22. The method of claim 18, wherein
the cassette holder includes a second shaft,
the cassette plate defines a second keyhole associated with a second channel of the cassette plate,
said moving the lever of the cassette plate from the locked position to the unlocked position includes also moving a second lever associated with the second channel of the cassette plate from a locked position in which the second lever is primarily positioned within the second channel to an unlocked position in which the second lever is primarily positioned outside of the second channel,
said moving the cassette plate with respect to the shaft includes moving the cassette plate with respect to the second shaft so as to move a perimeter groove of the second shaft from the necked down portion of the second keyhole to an open portion of the second keyhole, and
said moving the cassette plate away from the shaft includes moving the cassette plate away from the second shaft so as to cause a head of the second shaft to move through the open portion of the second keyhole.

23. The method of claim 18, wherein
the cassette holder includes a standalone shaft,
the cassette plate defines a standalone keyhole not associated with any channel or lever of the cassette holder,
said moving the cassette plate with respect to the shaft includes moving the cassette plate with respect to the standalone shaft so as to move a perimeter groove of the standalone shaft from the necked down portion of the standalone keyhole to an open portion of the standalone keyhole, and
said moving the cassette plate away from the shaft includes moving the cassette plate away from the standalone shaft so as to cause a head of the standalone shaft to move through the open portion of the standalone keyhole.

* * * * *